United States Patent [19]

Lauterbach et al.

[11] Patent Number: 4,990,284
[45] Date of Patent: Feb. 5, 1991

[54] MOISTURE INDICATING INK AND PACKAGE HAVING SAME

[75] Inventors: John H. Lauterbach; Carl B. Jenkins, both of Louisville, Ky.

[73] Assignee: Brown & Williamson Tobacco Corporation, Louisville, Ky.

[21] Appl. No.: 419,797

[22] Filed: Oct. 11, 1989

[51] Int. Cl.⁵ .................................. G01N 31/00
[52] U.S. Cl. .................... 252/408.1; 73/73; 106/20; 252/963
[58] Field of Search ............. 106/20, 21, 22, 27, 106/14.5; 116/206; 206/459; 252/408.1, 963; 430/126, 138; 428/86, 187; 436/41; 73/28, 29, 73

[56] References Cited

U.S. PATENT DOCUMENTS

| | | |
|---|---|---|
| 3,533,277 | 10/1970 | Krause ............................. 252/963 |
| 3,723,349 | 3/1973 | Heseltine ....................... 252/408.1 |
| 3,898,172 | 8/1975 | Reif ..................................... 116/206 |
| 4,045,397 | 8/1977 | Parkinson ....................... 252/408.1 |
| 4,179,397 | 12/1979 | Rokowetz et al. ............. 252/408.1 |
| 4,216,283 | 8/1980 | Cooper et al. ..................... 430/126 |
| 4,389,503 | 6/1983 | Maxwell et al. .................... 106/22 |
| 4,643,122 | 2/1987 | Seybold ............................... 436/41 |
| 4,793,264 | 12/1988 | Lin et al. ............................ 106/27 |
| 4,869,532 | 9/1989 | Abe et al. ........................... 106/20 |

Primary Examiner—John S. Maples
Assistant Examiner—Shean C. Wu
Attorney, Agent, or Firm—Charles G. Lamb

[57] ABSTRACT

A solution-type moisture indicating ink to be printed on a substrate and change color at a preselected ambient moisture. The indicator ink includes a solvent carrier system, a moisture indicating substance which changes color under the influence of moisture, and a resin system as a binder to hold the moisture indicating substance to the substrate as well as a film forming and viscosity adjusting agent.

29 Claims, 2 Drawing Sheets

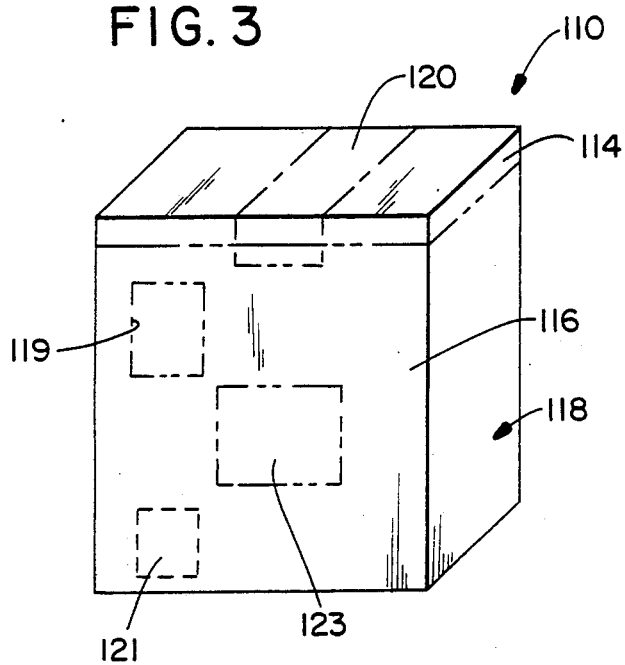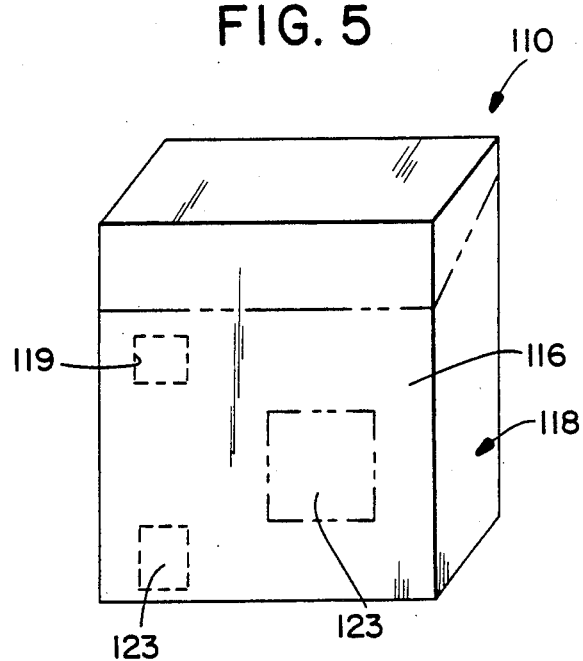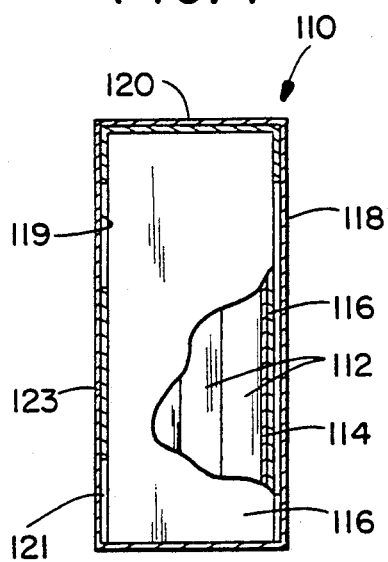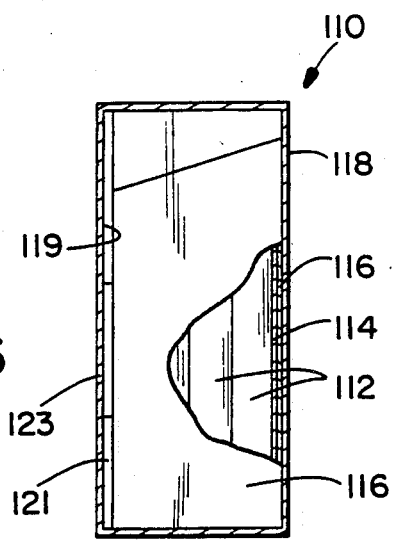

MOISTURE INDICATING INK AND PACKAGE HAVING SAME

BACKGROUND OF THE INVENTION (1) Field of the Invention

The present invention relates to inks which include an ingredient which changes color in response to different ambient moisture levels, and more particularly to a solution-type moisture indicating ink wherein the ink ingredients are in solution and which can be printed at a high rate upon the substrate.

(2) Discussion of the Prior Art

Various inks or coating which change color are known per se. Examples of such heretofore known and their uses are disclosed in the following United States Patents.

U.S. Pat. No. 650,901, issued on June 5, 1900 to Ernest Kretschmann.

U.S. Pat. No. 2,228,033, issued on Jan. 7, 1941 to Thomas A. Martone.

U.S. Pat. No. 3,216,802, issued on Nov. 9, 1965 to Charles J. Smith.

U.S. Pat. No. 3,360,339, issued on Dec. 26, 1967 to Martin Edenbauum.

U.S. Pat. No. 3,499,316, issued on Mar. 10, 1970 to W. O. Krause.

U.S. Pat. No. 3,548,639, issued on Dec. 22, 1970 to W. O. Krause.

U.S. Pat. No. 3,881,873, issued on May 6, 1975 to Iris B. Klowden.

U.S. Pat. No. 4,643,122, issued on Feb. 17, 1987 to Paul G. Seybold.

U.S. Pat. No. 650,901 teaches an ink consisting of a solution of the halide salts of cobalt, glycerin, gum arabic and water. A paper is coated with this solution. This ink is developed using a developing ink of resorcinol and paratoluidine, water, and sulfuric acid.

U.S. Pat. No. 2,228,033 teaches an ink which is normally invisible when printed on fabrics and paper, but becomes visible when wetted with a solution. This patent more particularly teaches cellulose nitrate or acetate or various gums and solvents such as amyl alcohol, butyl alcohol, their esters, and, glycol ethers. The ink also includes a colorless gum or resin or cellulose derivative in a volatile water soluble monohydric alcohol, preferably, ethyl cellulose in methyl or ethyl alcohol. When the ink is printed on paper, it is invisible, and becomes visible when wetted by water. The ink consists of a volatile alcohol of the group consisting of methyl and ethyl alcohol, and alcohol soluble cellulose ether.

U.S. Pat. No. 3,216,802 teaches a reagent for determining the moisture content of paper. The reagent is a solution of cobaltous chloride in a non-aqueous volatile solvent which is placed in contact with a fibrous web (such as paper) and the solvent allowed to evaporate so that the residue of cobaltous chloride remaining on the fibrous web will undergo a color change which is directly related to the moisture content of the fibrous web. The solvent may be methanol, ethanol, acetone or mixtures thereof.

U.S. Pat. No. 3,360,339 teaches a temperature indicating ink which consists of a solution of copper sulfite and a film such as methyl isobutyl ketone. The ink changes color when exposed to moisture above 250° F.

U.S. Pat. No. 3,499,316 teaches a moisture indicating material applied to a mat of inert fibers or paper and discloses the use of cobaltous bromide, magnesium chloride, calcium chloride, aluminum chloride and cobalt chloride as moisture indicators. The indicator of this ink uses a dual salt such as a cobaltous bromide and a bromide salt of zinc, cadmium or mercury as the moisture indicator which changes color.

U.S. Pat. No. 3,548,639 is related to U.S. Pat. No. 3,499,316 and teaches a dual salt moisture indicator of cobaltous bromide and barium chloride or magnesium chloride.

U.S. Pat. No. 3,881,873 teaches a moisture indicator of an aqueous solution of cobaltous chloride.

While the above patents discuss various moisture indicating inks which change color using cobalt chloride as the color changing ingredient or moisture indicator, alcohol as a carrier, and cellulose derivatives as a binder, none of these inks have been found suitable for use as a printing ink on commercial printing or coating equipment at production speeds. Furthermore, none of the heretofore color indicating inks known to us can be applied to a hydrophobic surface such as a glossy or top coated paper.

SUMMARY OF THE INVENTION

It is an object of the present invention to provide a moisture indicating ink which is suitable for use with high speed printing and coating equipment at production speeds.

It is another object of the present invention to provide a moisture indicating ink which can be printed or applied to a hydrophobic surface.

It is still another object of the present invention to provide a moisture indicating ink to be applied to the exterior surface of a package containing a tobacco product overwrapped by a transparent substantially moisture impervious film of, for example, polypropylene or cellophane, or the like, such as a cigarette package, which changes color at a preselected moisture level corresponding to a predetermined moisture content of the packaged tobacco products therein providing a quick visible indication of the freshness of the packaged tobacco product without the need to open the package.

More particularly, in one embodiment, the present invention provides a solution-type indicating ink comprising (a) a solvent carrier system said system including a compound selected from the group consisting of water, alcohol, an acetate ester, acetone, and combinations thereof, (b) a moisture indicating material which changes color at a preselected moisture level including cobaltous chloride; (c) a resin system as a binder to bond the cobaltous chloride to a substrate upon which the ink is to be deposited, said system including a film forming and viscosity adjusting agent selected from the group consisting of cellulose nitrate, polyvinyl alcohol, cellulose acetate, cellulose acetate propionate, cellulose acetate butyrate, poly (vinyl ether) ester, and poly (vinyl ether); and, (d) a color shift reagent, said color shift reagent adjusting preselected moisture level at which the cobaltous chloride changes color said color shift reagent including a compound selected from the group consisting of calcium chloride, polyethylene glycol, lithium chloride, aluminum chloride, a condensate of alkylphenol with ethylene oxide, sucrose, and combinations thereof.

In another embodiment, the present invention provides a package for articles comprising a sealed moisture impermeable transparent outer closure wrapper enclosing the articles, and a moisture indicating ink applied to the interior surface of the sealed outer closure so that it is exposed to the air trapped inside the sealed outer closure, and is visible through the outer closure, the ink being formulated to change color at a relative humidity of the air trapped by the outer closure corresponding to a predetermined moisture content of the articles.

In still another embodiment, the present invention provides a package for articles comprising a sealed moisture impermeable transparent closure wrapper enclosing the articles, a substrate disposed inside the sealed closure, and a moisture indicating ink applied to the substrate so that the ink is exposed to the air trapped inside the sealed closure and is visible through the outer closure, the ink being formulated to change color at a relative humidity of the air trapped by the outer closure corresponding to a predetermined moisture content of the articles.

In yet another embodiment, the present invention provides a package for articles comprising an inner wrapper enclosing the articles, a sealed moisture impermeable transparent outer closure wrapper enclosing the inner wrapper enclosure, and a moisture indicating ink applied to the interior surface of the sealed enclosure so that it is exposed to the air trapped inside the sealed outer closure, and is visible through the sealed outer enclosure, the ink being formulated to change color at a relative humidity of the air trapped by the outer closure corresponding to a predetermined moisture content of the articles.

In still yet another embodiment, the present invention provides a package for articles comprising an inner wrapper enclosing the articles, a sealed moisture impervious transparent outer closure wrapper enclosing the inner wrapper enclosure, a substrate disposed inside the sealed outer closure and outside the inner wrapper enclosure, and a moisture indicating ink applied to the substrate so that it is exposed to all trapped inside the sealed outer closure and is visible through the outer sealed closure, the ink being formulated to change color at a predetermined relative humidity of the air trapped inside the sealed closure corresponding to a predetermined moisture content of the articles inside the inner wrapper enclosure.

BRIEF DESCRIPTION OF THE DRAWINGS

A better understanding of the invention will be had upon reference to the following description in conjunction with the accompanying drawings wherein like numerals refer to like parts throughout the several views and in which:

FIG. 3 is a perspective view of still another package embodying the present invention;

FIG. 4 is a cross-sectional view of the package of FIG. 3;

FIG. 5 is a perspective view of yet another package embodying the present invention; and, FIG. 6 is a cross-sectional view of the package of FIG. 5.

DETAILED DESCRIPTION OF THE PREFERRED EMBODIMENTS

Figure 1:
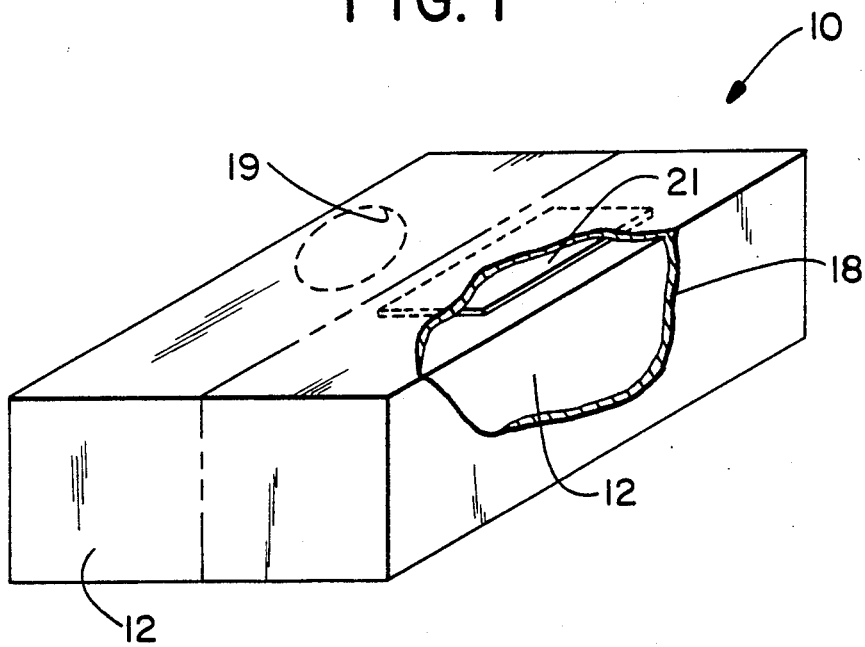
FIG. 1 is a perspective view with portions broken away to show internal details of a package embodying the present invention.

The solvent-type moisture indicating ink of the present invention is particularly adapted for printing onto a substrate, such as paper, using commercial printing techniques and equipment at high production speeds.

The moisture indicating ink comprises a liquid solvent carrier in which the other ink ingredients are dissolved, an active moisture indicating ingredient which changes color at a preselected moisture level, a resin system which functions as a film forming agent, a viscosity adjusting agent, and a binder to bond the moisture indicating ink to the substrate when the solvent carrier has evaporated. Optionally, a color shift reagent to adjust the predetermined moisture level at which the moisture indicating ingredient changes color is included. Also, a slip agent which reduces the friction between ink printed on the substrate and the printing equipment can be included in the ink.

The solvent carrier system is a substance which readily dries or evaporates. Such solvent carriers include water, an alcohol, an acetate ester, acetone, and combinations thereof. The preferred alcohols are propanol, isopropanol ethanol, or methanol. Di-methyl ketone can also be used as a preferred solvent carrier.

The active moisture indicating substance is preferably a cobalt compound. Cobaltous chloride has been found to be the most desirable of the cobalt compounds, because of its color qualities and stability over time. However, bromine compounds of cobalt may also be used.

The following Table I shows the results of a study of various active visual moisture indicators. This study was directed to finding compounds which would change color when the relative humidity was decreased from approximately 76% to approximately 44%. In this study, test papers were prepared by saturating filter paper (Whatman #1) with solutions of various test compounds and allowing the saturated filter papers to air dry. The treated filter papers were exposed to a range of relative humidities (RH) for at least 16 hours, and the color produced at each RH was observed and recorded. The RH values tested were 76%, 58%, 52%, and 44% at 25° C. These particular RM values were chosen because in the cigarette package an RH of 60% corresponds to a tobacco moisture content of cigarettes in the package of above 12% and an RM of 50% corresponds to a tobacco moisture content of cigarettes in the package of below 12%.

TABLE I

| | STUDY OF POTENTIAL VISUAL MOISTURE INDICATORS | | | |
|---|---|---|---|---|
| | COLOR DEVELOPED | | | |
| COMPOUNDS | 44% RH | 52% RH | 58% RH | 76% RH |
| Cobaltous Bromide | Dark Pink | | | Light Pink |
| Cobaltous Chloride | Blue & Trace Pink | Blue & Pink | Pink & Trace Blue | Pink |
| Cobaltous Iodine | Light Brown | Brown & Pink | Pink | Pink |
| Cobaltous Thiocyanate | Blue | Dark Blue | Dark Blue | Lavender |
| Cobaltous Acetate | Mulberry | NO CHANGE | | |
| Rhodium Sulfate | Yellow | NO CHANGE | | |
| Praseodymium Sulfate | White | NO CHANGE | | White & Trace |

TABLE I-continued

STUDY OF POTENTIAL
VISUAL MOISTURE INDICATORS

| COMPOUNDS | COLOR DEVELOPED | | | |
|---|---|---|---|---|
| | 44% RH | 52% RH | 58% RH | 76% RH |
| | | | | Green |

Because the results of the above survey or study indicated that cobaltous chloride was preferably for use as an active moisture indicator for an ink usable with cigarette packages, a study was conducted to determine the influence of the concentration of cobaltous chloride in a solution. Tests strips were prepared by saturating paper (Whatman #1) with aqueous solutions of cobaltous chloride at various concentrations. The test strips were air dried and exposed to various relative humidities. After overnight equilibration at 76%, 58%, 52%, and 44% RH, the color of the test strips were observed and recorded in the following Table II. As shown in Table II, the intensity of the color increased with increasing cobaltous chloride concentrations.

TABLE II

INFLUENCE OF CONCENTRATION
ON COLOR DEVELOPMENT

| CONCEN-TRATION OF CoCl2 SOL. | Color Developed | | | |
|---|---|---|---|---|
| | 44% RH | 52% RH | 58% RH | 76% RH |
| 10% | Blue & Trace Pink | Purple & Light Pink | Light Pink & Purple | Light Pink |
| 20% | Blue | Purple | Light Purple | Pink |
| 40% | Deep Blue | Deep Purple | Deep Purple | Dark Pink |

As a further step in the study toward developing the ink of the present invention, various salts and polymers were added to the cobaltous chloride solution used in the survey of cobaltous chloride concentrations discussed above in regard to Table II. The purpose of adding different salts was to determine their effect on changing the trigger point, i.e., the RH at which the cobaltous chloride changed from pink to blue. The purpose of testing different polymers was to determine the best ones for providing film forming properties and also the viscosity needed for proper application of the ink to the substrate using conventional printing equipment operated at high production speeds. The results are summarized in Table III below.

TABLE III

THE INFLUENCE OF ADDITIVES ON COBALTOUS
CHLORIDE COLOR DEVELOPMENT

| TEST MIXTURES | RELATIVE HUMIDITIES | | | |
|---|---|---|---|---|
| | 44% | 52% | 58% | 76% |
| $CoCl_2$ in supernatant liquid of aqueous poly (vinyl acetate) emulsion. (NS 1088-National Starch & Chemical Corp.) | Dark Blue | Not Tested | Deep Purple | Dark Rose |
| 1 g. $CoCl_2$ + 1 g. $CaCl_2$ + 10 g. aqueous poly (vinyl acetate) emulsion. (NS 1088) | Blue Green | Blue Green | Blue Gray | Pink |
| 1 g. $CoCl_2$ + 10 g. aqueous poly (vinyl acetate) emulsion. (NS 1088) | Purple | Purple & Pink | Pink & Purple | Pink |
| 1 g. $CoCl_2$ + 1 g. KCl + 10 g. aqueous poly (vinyl acetate) emulsion. (NS 1088) | Dark Blue | Light Blue | Purple | Pink |
| $CoCl_2$ in Joncryl Ink Formulation (Supplied by S. C. Johnson & Sons, Inc.). Solids ppt. on mixing. | Blue | Blue/ Purple | Purple | Pink |
| 1 g. $CoCl_2$ + 10 g. $H_2O$. | Light Blue | Pink** | Pink** | Pink |
| 1 g. $CoCl_2$ + KCl + 10 g. $H_2O$. | Light Blue-Gray | Light Purple | Light Pink-Purple | Pink |
| 1 g. $CoCl_2$ + 1 g. $CaCl_2$ + 10 g. $H_2O$. | Blue-Green** | Light Blue-Gray | Light Gray | Pink |
| 2 g. $CoCl_2$ + 1 g. $CaCl_2$ + 10 g. $H_2O$. | Blue | Light Blue | Light Purple | Pink |
| 1 g. $CoCl_2$ + 1 g. Gelatin + 10 g. $H_2O$. | Light Blue | Light Blue | Light Blue | Pink |
| 2 g. $CoCl_2$ + 1.3 g. Gelatin + 10 g. $H_2O$. | Dark Blue | Light Blue | Light Blue | Pink |
| 2 g. $CoCl_2$ + 1.3 g. Gelatin + 1 g. $CaCl_2$ + 10 g. $H_2O$. | Vivid Dark Blue | Dark Blue | Blue | Rose |
| 2 g. $CoCl_2$ + 10 g. aqueous poly (vinyl acetate) emulsion. (NS 1088) | Dark Blue | Purple | Light Purple | Pink-Rose |
| 0.5 g. $CoCl_2$ + 10 g. aqueous poly (vinyl | Light Pink | NO CHANGE | | |

TABLE III-continued
THE INFLUENCE OF ADDITIVES ON COBALTOUS CHLORIDE COLOR DEVELOPMENT

| TEST MIXTURES | RELATIVE HUMIDITIES | | | |
|---|---|---|---|---|
| | 44% | 52% | 58% | 76% |
| acetate) emulsion. (NS 1088) | | | | |
| 0.2 g. CoCl$_2$ + 10 g. aqueous poly (vinyl acetate) emulsion. (NS 1088) | NO COLOR DETECTED | | | |
| 0.2 g. CoCl$_2$ + 1 g. BaCl$_2$ + 10 g. H$_2$O. | Blue | Purple | Mulberry | Pink |
| 0.2 g. CoCl$_2$ + 2 g. BaCl$_2$ + 10 g. of 5% Gelatin. | Blue | Light Blue | Blue-Gray | Pink |
| 0.2 g. CoCl$_2$ + 2 g. BaCl$_2$ + 10 g. of H$_2$O | Blue | Purple | Pink-Purple | Pink |

*All CoCl$_2$ was added as CoCl$_2$.6H$_2$O
**Some spotting was noted as these samples aged The above test results show that cobaltous chloride is compatible with a large number of substances, and that the color development of the cobaltous chloride at a given relative humidity can be modified.

The resin system performs a multiplicity of functions. The resin system functions as a binder to bond the moisture indicating substance to the substrate upon which the ink is to be deposited. The resin system further functions as a film forming agent and also to increase the viscosity of the ink. Various resin systems were formulated and studied in different preferred solvent systems. The results are shown in Table IV below.

TABLE IV

| RESIN SYSTEM | COMMENTS* |
|---|---|
| Cellulose acetate | Propanol-2 and ethyl acetate solvent system; 11 cps. viscosity |
| CAP 504-0.2** cellulose acetate propionate and Nevillac 10XL (phenolic resin) | Ethyl alcohol and ethyl acetate solvent system; gave good colors. |
| CAP 504-0.2** cellulose acetate propionate and ink Beckacete 24-152 (phenolic resin) | Ethyl alcohol and ethyl acetate solvent system; gelled during formulation. |
| CAP 504-0.2** cellulose acetate propionate and Duco-Tak 80-2434 (acrylic resin) | Ethyl alcohol and ethyl acetate solvent system; 24 sec. viscosity; test prints pink at 60% RH, blue at 51% RH. |
| CAP 482-0.5** cellulose acetate propionate and Nevillac 10XL (phenolic resin) | Ethyl alcohol and ethyl acetate solvent system; 20 sec. viscosity; test prints light mulberry at 60% RH, blue at 51%. |
| CAP 482-0.5** cellulose acetate propionate and UNIREZ 7024 (maleic resin) | Ethyl alcohol and ethyl acetate solvent system; 26 sec. viscosity; test prints light lavender at 60% RH, blue at 51%. |
| CAB 381-0.5** cellulose acetate butyrate and and UNIREZ 7024 (maleic resin) | Ethyl alcohol and ethyl acetate solvent system; 24 sec. viscosity; test prints violet at 60% RH, blue at 52%. |
| GANTREZ ES 225 Poly (vinyl methyl) ether) ester | Ethyl alcohol and ethyl acetate solvent system; 21 sec. viscosity; test prints purple at 60% RH, blue at 51%. |
| GANTREZ M 154 Poly (vinyl methyl ether) | Ethyl alcohol and ethyl acetate solvent system; 24 sec. viscosity; test prints pink at 60% RH, blue at 51%. |

*Viscosities were determined with a #2 Zahn cup at 77° F. unless otherwise noted.
**In the above Table IV, CAP 504-0.2 is cellulose acetate propionate; CAP 482-0.5 is cellulose acetate propionate; and CAB 381-0.5 is cellulose acetate butyrate. These cellulose esters were purchased from Eastman Kodak Company. The important properties differentiating these various cellulose esters from each other are set forth in Table V below.

TABLE V

| Eastman Code No. | Viscosity Seconds | Viscosity Poises | Acyl Content Acetyl % | Acyl Content Butyryl % | Hydroxyl Content % | Melting Range °C. | Tg. °C. | Tukon Hardness Knoops | Weight/Volume lb/U.S. Gal | Weight/Volume Kg/L | Number Average Molecular Weight, MW$_N$ | Comments |
|---|---|---|---|---|---|---|---|---|---|---|---|---|
| CAB-381-0.5 Cellulose Acetate Butyrate | 0.5 | 1.9 | 13.0 | 37 | 1.5 | 155–165 | 130 | 12 | 10.00 | 1.20 | 30,000 | Application found in lacquers of all types. |

| Eastman Code No. | Viscosity Seconds | Viscosity Poises | Acetyl Content % | Combined Propionyl Content % | Hydroxyl Content % | Melting Range °C. | Tg. °C. | Tukon Hardness Knoops | Weight/Volume lb/U.S. Gal | Weight/Volume Kg/L | Number Average Molecular Weight, MW$_N$ | Comments |
|---|---|---|---|---|---|---|---|---|---|---|---|---|
| CAP-482-0.5 Cellulose Acetate Propionate | 0.5 | 1.9 | 2.5 | 45 | 2.8 | 188–210 | 142 | 13 | 10.20 | 1.22 | 25,000 | Low odor. Useful in printing inks, paper coatings, and cloth coatings. |

TABLE V-continued

| | | | | | | | | | | | |
|---|---|---|---|---|---|---|---|---|---|---|---|
| CAP-504-0.2 Cellulose Acetate Propionate | 0.2 | 0.76 | 2.5 | 40 | 5.0 | 188–210 | 159 | 12 | 10.53 | 1.26 | 15,000 | Excellent grease barrier properties. Low odor. Performs well in flexographic and rotogravure inks. Soluble in alcohol/water blends. Forms stable one-package thermoset systems. Excellent grease barrier properties. |

Various moisture indicating inks were formulated as shown in the following examples.

EXAMPLE I

Water as the solvent system (approximately 350 ml) was blended with cobaltous chloride hexahydrate (450g) as the moisture indicating ingredient, and vinyl-acrylic latex (350g) as the resin system. The vinyl-acrylic latex was "Resyn 25-2833" purchased from National Starch & Chemical Company. The viscosity of the ink was 22.82 sec., #2 Zahn cup. The ink was applied to CIS paper. At 60% RM, the ink was a very light pink (almost white), and at 53% RH the ink was blue.

EXAMPLE II

A solvent system of l-propanol (540g) was blended with cobaltous chloride hexahydrate (227g) and cellulose acetate propionate (CAP-504-0.2, 40g) as the resin system. The viscosity of the ink was 20.7 sec., #2 Zahn cup. The ink was applied to CIS paper. At 60% RM the ink was violet, and at 53% RM the ink was blue.

EXAMPLE III

Water as the solvent system (approximately 350 ml) was blended with poly (vinyl alcohol) (100% hydrolyzed; molecular weight 115.000;8g), and cobaltous chloride hexahydrate (51.2g) as the moisture indicating ingredient. The viscosity of the ink was 36 cps (brookfield RVT, #1 spindle). The ink was applied to CIS paper. At 76% RH the ink was pink, at 58% RM the ink was light lavender, at 52% RM the ink was deep purple, and at 44% RH the ink was dark blue.

EXAMPLE IV

A solvent system of 2-propanol (200ml) and l-propanol (50 ml) was blended with polyethylene glycol (5g) as the resin system, and cobaltous chloride anhydrous (13g) as the moisture indicating ingredient. The viscosity of the ink was 22 cps (Brookfield RVT, #1 spindle). The ink was applied to CIS paper. At 76% RM the ink was a faint pink, at 58% RM the ink was a pink-lavender color, at 52% RH the ink was lavender, and at 44% RM the ink was blue-lavender The most visually distinctive color for cobaltous chloride is the blue developed when it is dry compared with the lavender color when it has absorbed some moisture, and the pink color when it is fully hydrated. Various color shift reagents were tested in inks of the present invention having a solvent system comprising alcohol and ethyl acetate, and a resin system comprising cellulose acetate propionate, and cobaltous chloride as the active moisture indicating substance to determine the most effective reagent for adjusting the triggerpoint of the indicator ink so the ink would change to the more visually distinctive blue color at about 50% relative humidity. The following Table VI shows the results of these tests.

TABLE VI

| | COLOR SHIFT REAGENTS |
|---|---|
| Reagent | Ink and Comments |
| Calcium Chloride 15 weight percent of ink formulation | Mixed in ink comprising ethyl alcohol (21.9 kg) and ethyl acetate (5.5 kg) solvent system; CAP 482-0.5 cellulose acetate propionate (1.4 kg) and maleic resin (2.8 kg) as the resin system; and cobaltous chloride (8.8 kg). Shifts color of cobaltous chloride to blue. |
| Lithium chloride 5 weight percent of ink formulation | (a) Mixed in ink comprising ethyl alcohol (21.8 kg) and ethyl acetate (5.5 kg) solvent system; CAP 482-0.5 cellulose acetate propionate (1.4 kg) and maleic resin (8.8 kg) as the resin system; and cobaltous chloride. Produced little blue shift. (b) Mixed in ink comprising ethyl alcohol (22.0 kg) and ethyl acetate (4.8 kg) solvent system; CAP 504-0.2 cellulose acetate propionate (2.6 kg) and acrylic resin (2.2 kg) as the resin system; and cobaltous chloride (8.8 kg). Produced little blue shift. |
| Aluminum chloride hexahydrate 5 weight percent of ink formulation | (a) Mixed in ink comprising ethyl alcohol (21.9 kg) and ethyl acetate (5.5 kg) solvent system, CAP 482-0.5 cellulose acetae propionate (1.4 kg) and maleic resin (2.8 kg) as the resin system; and cobaltous chloride (8.8 kg). Produced blue shift. |

TABLE VI-continued
COLOR SHIFT REAGENTS

| Reagent | Ink and Comments |
|---|---|
| | (b) Mixed in ink comprising ethyl alcohol (22.0 kg) and ethyl acetate (4.8 kg) solvent system; CAP 504-0.2 cellulose acetate propionate (2.6 kg) and acrylic resin (2.2 kg) as the resin system; and cobaltous chloride (8.8 kg). Produced blue shift. |
| Magnesium chloride hexahydrate 5 weight percent of ink formulation | (a) Mixed in ink comprising ethyl alcohol (21.9 kg) and ethyl acetate (5.5 kg) solvent system; CAP 482-0.5 cellulose acetate propionate (1.4 kg) and maleic resin (2.8 kg) as the resin system; and cobaltous chloride (8.8 kg). No significant blue color shift noted.<br>(b) Mixed in ink comprising ethyl alcohol (22.0 kg) and ethyl acetate (4.8 kg) solvent system, CAP 504-0.2 cellulose acetate propionate (2.6 kg) and acrylic resin (2.2 kg) as resin system; and cobaltous chloride (8.8 kg). No significatn blue color shift noted. |
| Barium chloride dihydrate 5 weight percent of ink formulation | (a) Mixed with ink comprising ethyl alcohol (21.9 kg) and ethyl acetate (5.5 kg) solvent system; CAP 482-0.5 cellulose acetate propionate (1.4 kg) and maleic resin (2.8 kg) as resin system; and cobaltous chloride (8.8 kg). Insoluble and produced no significant blue color shift.<br>(b) Mixed with ink comprising ethyl alcohol (22.0 kg) and ethyl acetate (4.8 kg) solvent system; CAP 504-0.2 cellulose acetate propionate (2.6 kg) and acrylic resin (2.2 kg) as resin system; and cobaltous chloride (8.8 kg). Insoluble and produced no significant blue color shift. |
| Polyethylene glycol 3 weight percent of ink formulation | Mixed in ink comprising ethyl alcohol (22.0 kg) and ethyl acetate (4.8 kg) solvent system; CAP 504-0.2 cellulose acetate propionate (2.6 kg) and acrylic resin (2.2 kg) as resin system; and cobaltous chloride (8.8 kg). Significant blue color shift noted. |
| Polyethylene glycol 5 weight percent of ink formulation | Mixed in ink comprising ethyl alcohol (21.9 kg) and ethyl acetate (5.5 kg) solvent system; CAP 482-0.5 and maleic resin (1.4 kg) as the resin system; and cobaltous chloride (8.8 kg). More distinctive blue color shift noted than 3% used in ink resin CAP 504-0.2 cellulose acetate ester. |

From the above test, it was concluded that the preferred color shift reagents are polyethylene glycol in the ink comprising ethyl alcohol and ethyl acetate as the solvent system; CAP 482-0.5 cellulose acetate propionate and maleic resin as the resin system; and cobaltous chloride (hereinafter called "the type 1 ink") and, calcium chloride in the ink comprising ethyl alcohol and ethyl acetate as the solvent system; CAP 504-0.2 and acrylic resin as the resin system; and, cobaltous chloride (hereinafter called "the type 2 ink").

It is believed that in the type 1, the cellulose acetate propionate (CAP 482-0.5, Eastman Kodak) functions to increase the viscosity of the ink and acts as a film forming agent and binder, while the maleic resin functions to increase rub resistance and gloss of the ink after it has been applied to the substrate and dried. And, it is believed that in the type 2 ink, the cellulose acetate propionate (CAP 504-0.2, Eastman Kodak) functions to increase viscosity of the ink and acts as a film forming agent and binder, while the acrylic resin increases the viscosity of the ink, adds flexibility to the ink after it has been applied to the substrate and dried, and further helps bond the ink to the subtrate. However, it is realized that the functions for the compounds set forth for the type 1 and type 2 inks are not to be limitatively construed in the present invention.

It has been found advantageous to include a slip agent to reduce friction as the substrate (paper) upon which the ink is to be printed passes through the printing equipment, and downstream equipment which may be used to fold the substrate into a package. For example, a polyethylene works well as a slip agent in the type 1 and type 2 inks described above. For example, 1 to 3 weight percent of a finely micronized polyethylene (MPP-620 VF purchased from Micro Powders Inc.) processed to a NPIRI (National Printing Ink Research Institute) grind gauge reading of 2 to 2.5 (corresponding to Hegman 7.5) to both the type 1 and type 2 inks, and imparted excellent mar and rub resistance and surface slip to the printing inks. In another example, 1 to 3 weight percent of a finely micronized polyethylene (AQUA POLY 250 purchased from Micro Powders Inc.) processed to a NPIRI grind gauge reading of 3 to 4 (corresponding to Hegman 6.5 to 7.0) was used with good results.

EXAMPLE V

A first sample of a preferred embodiment of the type 1 ink of the present invention comprises 53.93 weight percent of ethyl alcohol, 13.46 weight percent of ethyl acetate, 21.58 weight percent cobaltous chloride, 3.48 weight percent of CAP 482 cellulose acetate propionate 6.96 weight percent maleic resin, and 0.59 weight percent of a slip agent such as polyethylene wax or polyethylene powder.

EXAMPLE VI

A first sample of a preferred embodiment of the type 2 ink of the present invention was formulated to 54.11 weight percent ethyl alcohol, 11.48 weight percent ethyl acetate, 21.65 weight percent cobaltous chloride, 6.43 weight percent CAP 504 cellulose acetate, 5.41 weight percent acrylic resin, and 0.56 weight percent of a slip agent such as polyethylene wax or polyethylene powder.

To test for discoloration (degradation) of the ink due to exposure to light, the type 1 and type 2 inks were printed on 60# ClS paper, and the paper was exposed to fluorescent light. The inks tended to discolor somewhat, and this discoloration became more evident as the amount of color shift reagent in the ink was increased. The type 1 and type 2 inks were further tested for discoloration by printing the ink on coated paper typically used in the industry to make cigarette packages as well as uncoated paper to test for any differences in discoloration due to the coating on the paper. The paper coating is typically a clay and a binder. These test samples were then exposed to fluorescent light as before and it was observed that the ink printed on the coated paper tended to discolor more than the ink printed on the uncoated paper. Both the type 1 and type 2 inks were printed on Whatman #1 filter paper, and exposed to fluorescent light. These samples did not appear to exhibit discoloration when exposed to flourescent light.

EXAMPLE VII

In a second sample of a preferred embodiment, the type 1 ink of the present invention was reformulated to obtain a more distinct color change and shift the color change point in the 50% to 60% relative humidity range by adding a color shift reagent of polyethylene glycol. This embodiment of the type 1 ink of the present invention comprised 49.33 weight percent ethyl alcohol, 12.31 weight percent ethyl acetate, 22.68 weight percent cobaltous chloride, 7.30 weight percent maleic resin, 3.65 weight percent cellulose acetate propionate (CAP 482), 4.07 weight percent polyethylene glycol. In addition, 0.56 weight percent of a slip agent (polyethylene) and 0.10 weight percent of an antioxidant (hydroquinone) to inhibit discoloration were included in this reformulated type 1 ink.

EXAMPLE VIII

In a second sample of a preferred embodiment, the type 2 ink of the present invention was reformulated to obtain a more distinct color change and shift the color change point in the 47% to 57% relative humidity range by adding a color shift reagent of calcium chloride. This embodiment of the type 2 comprised 45.11 weight percent ethyl alcohol, 20.49 weight percent ethyl acetate, 17.14 weight percent cobaltous chloride, 4.32 cellulose acetate propionate (CAP 504), 3.64 weight percent acrylic resin, 8.75 weight percent calcium chloride. In addition, 0.42 weight percent of a slip agent, for example polyethylene and 0.13 weight percent of an antioxidant (hydroquinone) to inhibit discoloration were included in the formulation.

EXAMPLE IX

In a third sample of a preferred embodiment, the type 2 ink comprised 45.37 weight percent ethyl alcohol, 20.03 weight percent ethyl acetate, 17.24 weight percent cobaltous chloride, 3.68 weight percent acrylic resin, 4.34 weight percent cellulose acetate, 8.79 weight percent calcium chloride, 0.42 weight percent slip agent (polyethylene), and 0.13 weight percent antioxidant (hydroquinone) to inhibit discoloration.

EXAMPLE X

In a fourth sample of a preferred embodiment, the type 2 ink comprised 44.08 weight percent ethyl alcohol, 18.40 weight percent ethyl acetate, 16.75 weight percent cobaltous chloride, 3.57 weight percent acrylic resin, 4.676 weight percent cellulose acetate, 8.54 weight percent calcium chloride, and 4.04 weight percent of an antioxidant to inhibit discoloration. The UV stabilizer and antioxidant comprised 0.13 weight percent Irganox 1076, a UV stabilizer manufactured by Ciba-Geigy, and 3.91 weight percent hydroquinone.

EXAMPLE XI

In a fifth sample of a preferred embodiment, the type 2 ink comprised 23.8 grams of ethyl acetate and 108.9 grams of ethanol, 12.8 grams of cellulose acetate propionate (CAP-504.4-0.2) 6.25 grams of polyethylene glycol (6000MW), 5 grams of water, 50.9 grams of cobaltous chloride (anhydrous), 1.24 grams of finely micronized polyethylene, and 0.4 grams of Irganox, a UV stabilizer manufactured by Ciba-Geigy. The viscosity of the ink was 32 seconds, #2 Zahn cup. This ink was applied to uncoated ClS paper. At 57% RH the ink was a light blue color, at 47% RM the ink was a dark blue color. This ink was also applied to ClS paper which was top-lacquered. At 57% RH the ink was a lavender color, and at 47% RM the ink was a blue color. This ink was further applied to a plastic film (Mylar). At 57% RH the ink was a light lavender color, and at 47% RH the ink was a blue color.

EXAMPLE XII

In a sixth sample of a preferred embodiment, the type 2 ink comprised 23.8 grams of ethyl acetate, 108.9 grams of ethanol, 12.8 grams of cellulose acetate propionate 6.25 grams of polyethylene glycol (6000MW), 5.0 grams water, 5.09 grams of cobaltous chloride (anhydrous), 1.24 grams of finely micronized polyethylene, 0.4 grams of Irganox 1076, and 1.0 grams of sucrose as a further color shift agent. This ink was applied to ClS paper. At 57% RM the ink was a light blue color, and at 47% RH the ink was a dark blue color. This ink was also applied to top lacquered ClS paper. At 57% RH the ink was a light blue color, and at 47% Rh the ink was a dark blue color. The ink was further applied to plastic film (Mylar). At 57% RH the ink was a light blue color, and at 47% RH the ink was a dark blue color.

The wave length of light responsible for discoloration was examined by printing Westvaco 60#ClS paper with the type 1 and type 2 inks (Examples VII to XII), and exposing the paper to fluorescent light with filters which block out certain wavelength ranges of light. The samples were exposed to fluorescent light for one week. The discoloration appeared to be caused primarily by light below 400 nanometers based on color measurements made with a Minolta colorimeter.

Irganox 1076 from Ciba-Geigy, which is a sterically hindered phenol was tested in the inks and it was observed that discoloration was reduced. Hydroquinone was tested in the inks at various concentrations of from 0.1% to 4.0%. It was found that hydroquinone was very effective in inhibiting discoloration at concentrations above 1.0%. It is believed that the hydroquinone is consumed as it protects the ink from discoloration.

Now with reference to FIG. 1, there is shown a package, generally denoted as the numeral 10, for containing articles 12. The package 10 includes a sealed outer closure 18 of transparent, substantially moisture impermeable material such as a transparent plastic material, for example, polypropylene film or cellophane and the like. The articles 12 can be virtually any material which is effected by moisture content of the articles 12. The package 10 of the present invention provides for disposing a moisture indicating ink, for example, the above described moisture indicating inks, between the sealed outer closure 18 and the packaged articles 12 so that the moisture indicating ink is exposed to the air trapped inside the sealed outer closure 18 and is visible through the sealed outer closure 18. The moisture indicating ink can be applied, or printed on the interior surface of the sealed outer closure 18 as indicated by the numeral 19, or can be applied, or printed on a substrate 21, such as a label, inserted or positioned between the articles 12 and the sealed outer closure 18. The moisture indicating ink is formulated to change color at a predetermined RH (relative humidity), or RH range, of the air trapped between the articles 12 and outer closure 18 corresponding to a predetermined moisture content, or moisture content range, of the articles 12. Therefore, the moisture content of the articles 12 can be determined at a glance by observing the color of the moisture indicating ink without having to open the package.

Figure 2:
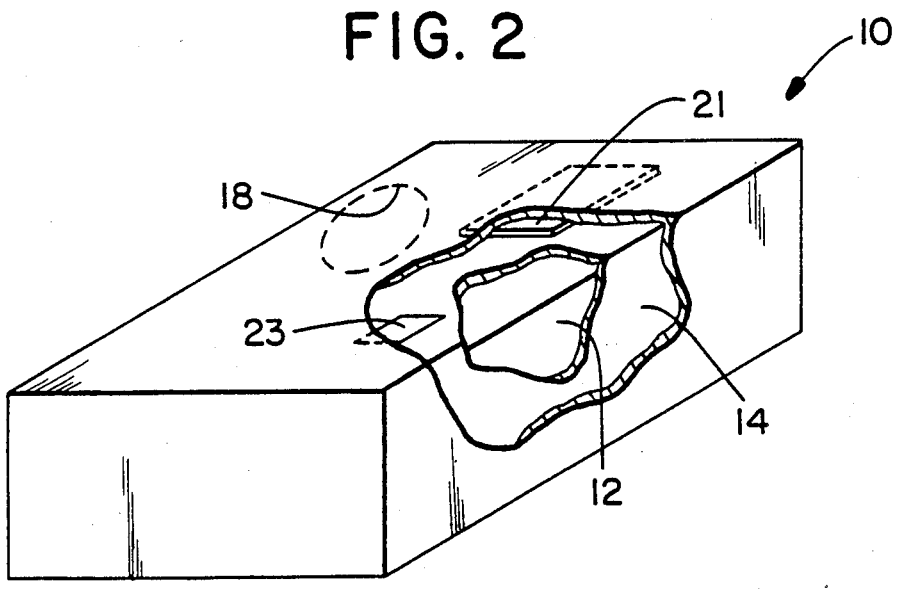
FIG. 2 is a perspective view, with portions broken away to show internal details of yet another package embodying the present invention.

FIG. 2 illustrates a modified package of FIG. 1 which is identical thereto except for the addition of an inner wrapper 14 enclosing the articles 12 beneath the sealed outer closure 18. All of the other components are identical to those of FIG. 1 and are denoted by identical numerals, therefore, for the sake of brevity, the description thereof will not be repeated. As with the embodiment of FIG. 1, the indicator ink can be applied to the interior side of the outer closure 18, as indicated by the number 18, or applied to a substrate 21, such as label 21, or applied directly on the outside surface of the inner wrapper 14 as indicated by the numeral 23.

Now, with reference to the FIGS. 2-5, there is shown another article package, such as a conventional cigarette package 110 for holding a plurality of cigarettes 112. A foil inner wrapper 114 encloses the cigarettes 112, and is folded over but not sealed at the top and bottom to form a foil bundle. An outer covering 116 encloses at least the sides of the inner foil wrapper 114. As shown in FIGS. 2 and 3, the outer covering 116 is a product label circumscribing the foil bundle. As shown in FIGS. 4 and 5, the outer covering 116 is a box of heavy paper known in the industry as a flip-open box. A sealed moisture impermeable outer closure 118, of a transparent plastic material, such as polypropylene film or cellophane, encloses the inner foil bundle 114 and outer covering 116 creating a closed environment and functions as a moisture carrier. Also, conventionally, a closure strip 120 is disposed across the top folded end of the inner foil bundle of the package 110 of FIGS. 2-3, or across the top of the flip top box type of outer covering 116 of FIGS. 4-5. The moisture of the air trapped inside the sealed outer covering 118 and the humidity of the cigarettes 112 inside the inner foil bundle 114 will reach equilibrium because of the fact that the foil wrapper 114 is folded, but not sealed. It is believed that the moisture of the tobacco of the cigarettes be at a predetermined level, for example, above 12% for good quality. It is desirable to be able to detect when the moisture if the cigarettes in the package 110 falls below or rises above this predetermined moisture level without opening the package 110. The cigarette package 110 of the present invention pr for the disposition of a moisture indicating ink, for example, the above described moisture indicating inks inside of the sealed outer closure 118 so that the moisture indicating ink is exposed to the air trapped inside the sealed outer closure 118 and is visible through the sealed outer closure 118 so that the moisture content of the cigarettes can be detected at a glance by observing the color of the moisture indicating ink without having to open the package 110. Toward this objective, the above described moisture indicating ink can be applied, or printed on the interior surface of the sealed outer enclosure 118 as indicated by the numeral 119, or on the outer covering 116, or on a substrate comprising, for example, the closure strip 120, or the outer covering 116 itself, or on an insert label 121 located between the outer covering 116 and sealed outer closure 118 so that it is exposed to the air trapped inside the sealed outer closure 118.

The relative humidity (RH) of the air trapped inside the sealed outer closure 118 is related to the moisture content of the tobacco of the cigarettes 112. For example, it has been found that a relative humidity of about 60% corresponds to a tobacco moisture content of above 12% and a relative humidity of about 50% corresponds to a tobacco moisture content below 12%. The color indicating ink can be formulated to change color at a predetermined RM, or RH range, of the air trapped by the outer closure 118 corresponding to a predetermined moisture content, or moisture content range, of the articles 112. It is an advantageous feature of the moisture indicating that by the use of a color shift reagent the relative humidity at which the ink changes color can be readily adjusted or changed to suit various predetermined tobacco moisture levels.

The foregoing detailed description is given primarily for understanding and no unnecessary limitations are to be understood therefrom for modifications will become obvious to those skilled in the art upon reading this disclosure and can be made without departing from the spirit of the invention or the scope of the appended claims.

What is claimed is:

1. A solution-type moisture indicating printing ink to be printed on a substrate at a high rate of speed, comprising:
   (a) a solvent carrier system selected from the group consisting of: water, alcohol, acetone, ethyl acetate, and, mixtures thereof;
   (b) a moisture indicating material including cobaltous chloride which changes color at a predetermined moisture level;
   (c) a resin system as a binder to bond the cobaltous chloride to a substrate upon which the ink is to be deposited, said system including a film forming and a viscosity adjusting agent selected from the group consisting of polyvinyl alcohol, cellulose acetate, cellulose acetate propionate, polyethylene glycol, cellulose acetate butyrate, vinyl-acrylic latex, poly(vinyl akyl) ester, and, poly(vinyl aklyl ether).

2. The solution-type moisture indicating ink of claim 1, further comprising: a color shift reagent to adjust the predetermined moisture level at which the cobaltous chloride changes color selected from the group consisting of sucrose, calcium chloride, polyethylene glycol, lithium chloride, aluminum chloride, condensate of alkylphenol with ethylene oxide, and, combinations thereof.

3. The solution-type moisture indicating ink of claim 1, wherein:

the solvent system comprises alcohol and ethyl acetate; and, the resin system comprises cellulose acetate.

4. The solution-type moisture indicating ink of claim 1, wherein the alcohol of the solvent system is propanol.

5. The solution-type moisture indicating ink of claim 1, wherein the resin system further comprises a compound selected from the group consisting of phenolic resin, acrylic resin, and, maleic resin.

6. The solution-type moisture indicating ink of claim 1, wherein:

the solvent system comprises an alcohol and ethyl acetate; and, the resin system comprises cellulose acetate, and phenolic resin.

7. The solution-type moisture indicating ink of claim 6, wherein the alcohol of the solvent system is ethyl alcohol.

8. The solution-type moisture indicating ink of claim 5, wherein:

the solvent system comprises alcohol and ethyl acetate; and, the resin system comprises cellulose acetate and acrylic resin.

9. The solution-type moisture indicating ink of claim 8, wherein the alcohol of the solvent system is ethyl alcohol.

10. The solution-type moisture indicating ink of claim 9, wherein the cellulose acetate of the resin system is cellulose acetate propionate.

11. The solution-type moisture indicating ink of claim 5, wherein:

the solvent system comprises alcohol and ethyl acetate; and, the resin system comprises cellulose acetate and maleic resin.

12. The solution-type moisture indicating ink of claim 11 wherein the alcohol of the solvent system is ethyl alcohol.

13. The solution-type moisture indicating ink of claim 12, wherein the cellulose acetate of the resin system is cellulose acetate propionate.

14. The solution-type moisture indicating ink of claim 12, wherein the cellulose acetate of the resin system is cellulose acetate butyrate.

15. The solution-type moisture indicating ink of claim 1, wherein:

the solvent system comprises alcohol and ethyl acetate; and, the resin system comprises poly(vinyl alkyl ether) ester.

16. The solution-type moisture indicating ink of claim 15, wherein the alcohol of the solvent system is ethyl alcohol.

17. The solution-type moisture indicating ink of claim 1, wherein:

the solvent system comprises alcohol and ethyl acetate; and, the resin system comprises poly(vinyl alkyl ether).

18. The solution-type moisture indicating ink of claim 17, wherein the alcohol of the solvent is ethyl alcohol.

19. The solution-type moisture indicating ink of claim 1, wherein the alcohol of the solvent system comprises propanol.

20. The solution-type moisture indicating ink of claim 1, wherein the color shift reagent is polyethylene glycol.

21. The solution-type moisture indicating ink of claim 1, wherein the color shift reagent is calcium chloride.

22. The solution-type moisture indicating ink of claim 1, further comprising a free radical stabilizer as a degradation inhibitor and antioxidant.

23. The solution-type moisture indicating ink of claim 22, wherein the degradation inhibitor and antioxidant comprises hydroquinone.

24. The solution-type moisture indicating ink of claim 1 further comprising a slip agent for reducing friction between a substrate to which the ink is being applied and the equipment applying the ink to the substrate.

25. The solution-type moisture indicating ink of claim 24, wherein the slip agent comprises polyethylene.

26. The solution-type moisture indicating ink of claim 25, wherein the slip agent is polyethylene wax.

27. The solution-type moisture indicating ink of claim 25, wherein the slip agent is micronized polyethylene powder.

28. The solution-type moisture indicating ink of claim 5, wherein the resin system comprises cellulose acetate propionate and maleic resin.

29. The solution-type moisture indicating ink of claim 5, wherein the resin system comprises cellulose acetate propionate and acrylic resin.

* * * * *

UNITED STATES PATENT AND TRADEMARK OFFICE
CERTIFICATE OF CORRECTION

PATENT NO. : 4,990,284                                    Page 1 of 3
DATED      : February 5, 1991
INVENTOR(S): John H. Lauterbach and Carl B. Jenkins It is certified that error appears in the above-identified patent and that said Letters Patent is hereby corrected as shown below:

Column 2, line 53, after "and viscosity" delete "adJusting" and insert therefor -- adjusting --.

Column 3, line 40, after "exposed to" delete "all" and insert therefor --air--.

Column 4, line 45, after "These particular" delete "RM" and insert therefor --RH--.

Column 4, line 48, after "and an" delete "RM" and insert therefor --RH--.

Column 9, line 30, after "At 60%" delete "RM" and insert therefor--RH --.

Column 9, line 38, after "At 60%" delete "RM" and insert therefor --RH--.

Column 9, line 39, after "at 53%" delete "RM" and insert therefor --RH--.

Column 9, lines 46 & 47, after "was 36 cps" delete "(brookfield" and insert therefor -- (Brookfield --.

Column 10, line 19, after "at 58%" delete "RM" and insert therefor --RH--.

Column 10, line 20, after "at 52%" delete "RM" and insert therefor --RH--.

Column 10, line 29, after "at 76%" delete "RM" and insert therefor --RH--.

UNITED STATES PATENT AND TRADEMARK OFFICE
CERTIFICATE OF CORRECTION

PATENT NO. : 4,990,284

DATED : February 5, 1991

INVENTOR(S) : John H. Lauterbach and Carl B. Jenkins

It is certified that error appears in the above-identified patent and that said Letters Patent is hereby corrected as shown below:

Column 10, line 30, after "At 58%" delete "RM" and insert therefor --RH--.

Column 10, line 32, after "44%" delete "RM" and insert therefor --RH--.

Column 11, second paragraph (b), line 5, after "(8.8kg). No" delete "significatn" and insert therefor -- significant--.

Column 12, line 58, after "acetate propionate" insert --,--.

Column 14, line 7, after "resin," delete "4.676" and insert therefor --4.626--.

Column 14, line 25, after "at 47%" delete "RM" and insert therefor --RH--.

Column 14, line 28, after "at 47%" delete "RM" and insert therefor --RH--.

Column 14, line 36, after "acetate propinate" insert --,--.

Column 14, line 42, after "57%" delete "RM" and insert therefor --RH--.

Column 15, line 43, after "bottom" insert --ends--.

Column 15, line 55, after "inner foil" insert --wrapped--.

Column 15, line 65, delete "if" and insert therefor --of--.

UNITED STATES PATENT AND TRADEMARK OFFICE
CERTIFICATE OF CORRECTION

PATENT NO. : 4,990,284

DATED : February 5, 1991

INVENTOR(S) : John H. Lauterbach and Carl B. Jenkins

It is certified that error appears in the above-identified patent and that said Letters Patent is hereby corrected as shown below:

Column 15, line 68, after "present invention" delete "pr" and insert therefor --provides--.

Column 16, line 25, after "can be formulated' delete "lo" and insert therefor --to--.

Column 16, line 26, after "predetermined' delete "RM" and insert therefor --RH--.

Column 16, line 30, after "moisture indicating" insert therefor --ink--.

Column 16, line 58, after "poly (vinyl" (second occurrence) delete "aklyl" and insert therefor --alkyl--.

Signed and Sealed this

Twenty-second Day of September, 1992

Attest:

DOUGLAS B. COMER

*Attesting Officer*   *Acting Commissioner of Patents and Trademarks*